United States Patent [19]
Dunn et al.

[11] Patent Number: 6,007,983
[45] Date of Patent: Dec. 28, 1999

[54] METHOD AND KIT FOR EVALUATION OF HIV MUTATIONS

[75] Inventors: James M. Dunn, Scarborough; Jean-Michel Lacroix, Etobicoke, both of Canada

[73] Assignee: Visible Genetics Inc., Toronto, Canada

[21] Appl. No.: 08/938,641

[22] Filed: Sep. 26, 1997

Related U.S. Application Data

[63] Continuation-in-part of application No. 08/577,858, Dec. 22, 1995, Pat. No. 5,834,189, and a continuation-in-part of application No. 08/819,912, Mar. 18, 1997, Pat. No. 5,795,722.

[51] Int. Cl.$^6$ ...................................................... C12Q 1/70
[52] U.S. Cl. ................................................. 435/5; 435/91.1
[58] Field of Search .............................. 435/5, 91.1, 810; 536/24.3, 24.32, 24.33

[56] References Cited

U.S. PATENT DOCUMENTS

| | | | |
|---|---|---|---|
| 4,358,535 | 11/1982 | Falkow et al. | 435/5 |
| 4,563,417 | 1/1986 | Albarella et al. | 435/6 |
| 4,683,195 | 7/1987 | Mullis et al. | 435/6 |
| 4,683,202 | 7/1987 | Mullis | 435/91 |
| 4,942,124 | 7/1990 | Church | 435/6 |
| 4,962,020 | 10/1990 | Tabor et al. | 435/6 |
| 5,008,182 | 4/1991 | Sninsky et al. | 435/5 |
| 5,124,247 | 6/1992 | Ansorge | 435/6 |
| 5,171,534 | 12/1992 | Smith et al. | 422/82.05 |
| 5,176,995 | 1/1993 | Sninsky et al. | 435/6 |
| 5,219,727 | 6/1993 | Wang et al. | 435/6 |
| 5,283,171 | 2/1994 | Manos et al. | 435/5 |
| 5,403,707 | 4/1995 | Atwood et al. | 435/5 |
| 5,409,810 | 4/1995 | Larder et al. | 435/5 |
| 5,427,911 | 6/1995 | Ruano et al. | 435/6 |
| 5,451,512 | 9/1995 | Apple et al. | 435/91.2 |
| 5,453,355 | 9/1995 | Birkenmeyer et al. | 435/6 |
| 5,545,527 | 8/1996 | Stevens et al. | 435/6 |
| 5,795,722 | 8/1998 | Lacroix et al. | 435/6 |
| 5,834,189 | 11/1998 | Stevens et al. | 435/6 |

FOREIGN PATENT DOCUMENTS

| | | |
|---|---|---|
| 9215711 | 9/1992 | WIPO . |
| 9219771 | 11/1992 | WIPO . |
| 9723650 | 7/1997 | WIPO . |

OTHER PUBLICATIONS

Larder et al., Nature 365, 671–673, 1993.

Sarkar et al., "Dideoxy Fingerprinting (ddF): A Rapod and Efficient Screen for the Presence of Mutations" *Genomics* 13: 441–443 (1992).

Lin et al., "Characterization of Genetic Defects of Hemophilia A in Patients of Chinese Origin" *Genomics* 18: 496–504 (1993).

Langemeir et al, "Application of Cycle Dideoxy Fingerprinting to Screening Heterogenous Populations of the Equine Infectious Anemia Virus", *BioTechniques* 17: 484–490 (1994).

Nelson et al., "Sequencing two DNA templates in five channels by digital compression", *Proc. Nat'l Acad/Sci.* (*USA*) 90: 1647–1651 (1993).

Ansorge et al., "One Label, one tube, Sanger DNA sequencing in one and two lanes on a gel", *Nucl. Acids Res.* 18: 3419–3420 (1990).

Negri et al., "A Single–Reaction Method for DNA Sequence Determinaiton" *Anal. Biochem* 197: 389–395 (1991).

Krishnamani et al., "Detection of a Novel Arginine Vasopressin Defect by Dideoxy Fingerprinting" *J. Clin. Endocrinol. & Metabol.* 77: 596–598 (1993).

Schinazi et al., "Mutation in retroviral genes associated with drug resistance", *Int'l Antiviral news* 5: 129–142 (1997).

Chamberlain et al., "Detection of Gene Deletions Using Multiplex Polymerase Chain Reactions", *Meth. Molec. Biol.* 9: 299–312 (1991).

Ellison et al., "Detection of Mutations and Polymorphisms Using Fluorescence–Based Dideoxy Fingerprinting (F–ddF)", *Biotechniques* 17: 742–753 (1994).

Eisenstein, B.I., "The Polymerase Chain reaction", *New Engl. J. Med.* 322: 178–183 (1990).

Murakawa et al., "Direct Detection of HIV–1 RNA from AIDS and ARC Patient Samples", *DNA* 7: 287–295 (1988).

Ruano et al., "Coupled Amplification and Sequencing of Genomic DNA", *Proc. Natl'l Acad Sci* (*USA*) 88: 2815–2819 (1991).

*Primary Examiner*—Kenneth R. Horlick
*Attorney, Agent, or Firm*—Oppedahl & Larson LLP

[57] ABSTRACT

A streamlined, hierarchical method for obtaining information about the allelic type of a sample of genetic material derived from an HIV-infected sample relies on the observation that 93–95% of the known mutational variants of the reverse transcriptase and protease genes of HIV-1 can be determined by evaluating the positions of the A and T nucleotides within the sample. Thus, a substantial fraction of all mutational variations can be unequivocally identified by performing two initial sequencing reactions on the sample in which only ddA and ddT are used as chain terminators. For the small fraction of samples which are not identifiable based on the positions of these two bases, a second test is performed in which the sequence is determined in the 3'-direction for all four bases. This test will identify substantially all of the remaining samples. For those for which an ambiguity remains, however, a final test in which the sequence of the sample is determined in both the 3' and 5-direction for all four bases is performed. To perform the method, reagents suitable for performing the three tests within the hierarchy are suitably packaged as a kit containing two or more sub-kits. The first sub-kit contains reagents for performing A and T sequencing. The additional sub-kits contains reagents for performing a four-base sequence determination on one or both strands of the target DNA.

15 Claims, 8 Drawing Sheets

HIV mutations-Protease Gene

| | A-T | A-G | A-C | G-A | G-C | G-T | C-A | C-G | C-T | T-A | T-G | T-C | | A | G | C | T |
|---|---|---|---|---|---|---|---|---|---|---|---|---|---|---|---|---|---|
| | | | | | | | | | | | | | | 65% | 59% | 35% | 41% |
| | | | | | | | | | | | | | | 30 | 27 | 16 | 19 |
| Protease Inhibitors | | | | | | | | | | | | | | | | | |
| R8Q | 3 | 5 | 3 | 12 | 1 | 3 | 4 | 2 | 1 | 3 | 4 | 5 | 46 | | | | |
| R8K | | | | 1 | | | | | | | | | 1 | A+T | G+C | | |
| L10F | | | | 1 | | | 1 | | | | | | 2 | 43 | 40 | | |
| L10I | | | | | | | | | | | | | 2 | 93% | 87% | | |
| L10R | | | | | | | 1 | 1 | | | | 1 | 1 | | | | |
| L10V | | | | | | | | 1 | | | 1 | | 1 | | | | |
| K20R | | | | | | | 1 | | | | | | 1 | | | | |
| K20M | 1 | | | 1 | | | | | | | | | 1 | | | | |
| L23I | | | | | | | | | | 1 | | | 1 | | | | |
| L24I | | | | | | | | | | | | | 1 | | | | |
| L24V | | | | | | | | | | | 1 | | 1 | | | | |

FIG 2A, part 1

| | A-T | A-G | A-C | G-A | G-C | G-T | C-A | C-G | C-T | T-A | T-G | T-C | |
|---|---|---|---|---|---|---|---|---|---|---|---|---|---|
| D30N | | | | 1 | | | | | | | | | 1 |
| V32I | | | | 1 | | | | | | | | | 1 |
| L33F | | | 1 | | | | | | | | | | 1 |
| M36I | | | | 1 | | | | | | | | | 1 |
| K45I | 1 | | | | | | | | | | | | 1 |
| M46I | | | | 1 | | | | | | | | | 1 |
| M46L | | | 1 | | | | | | | | | | 1 |
| M46F | 1 | | | | 1 | | | | | | | | 2 |
| I47V | | | 1 | | | | | | | | | | 1 |
| G48V | | | | | | 1 | | | | | | | 1 |
| I50V | | 1 | | | | | | | | | | | 1 |
| I54V | | 1 | | | | | | | | | | | 1 |
| D60E | | | | | | | | | | 1 | | | 1 |
| L63P | | | | | | | | | | | | 1 | 1 |
| A71V | | | | | | | | | 1 | | | | 1 |
| A71T | | | | 1 | | | | | | | | | 1 |
| V75I | | | | 1 | | | | | | | | | 1 |

FIG 2A, part 2

| | A-T | A-G | A-C | G-A | G-C | G-T | C-A | C-G | C-T | T-A | T-G | T-C | | |
|---|---|---|---|---|---|---|---|---|---|---|---|---|---|---|
| P81T | | | | | | | 1 | | | | | | | 1 |
| V82I | | | | 1 | | | | | | | | | | 1 |
| V82A | | | | | | 1 | | | | | | | | 1 |
| V82F | | | | | | 1 | | | | | | 1 | | 1 |
| V82S | | | | | | | | | | | | | | 2 |
| V82T | | | | 1 | | | | | | | | 1 | | 2 |
| I82T | | | | | | | | | | | | 1 | | 1 |
| I84V | | 1 | | | | | | | | | | | | 1 |
| I84A | | | | 1 | | | | | | | | | | 1 |
| N88D | | 1 | | | | | | | | | | | | 1 |
| N88S | | 1 | | | | | | | | | | | | 1 |
| L90M | | | | | | | | | | 1 | | | | 1 |
| L97V | | | | | | | | | | | 1 | | | 1 |

FIG 2A, part 3

HIV mutations-RT Gene

| | A-T | A-G | A-C | G-A | G-C | G-T | C-A | C-G | C-T | T-A | T-G | T-C | | A | G | C | T | | A+T | G+C |
|---|---|---|---|---|---|---|---|---|---|---|---|---|---|---|---|---|---|---|---|---|
| | 7 | 10 | 6 | 12 | 3 | 2 | 3 | 0 | 3 | 6 | 4 | 3 | 59 | 75% | 53% | 31% | 42% | | 95% | 78% |
| | | | | | | | | | | | | | | 44 | 31 | 18 | 25 | | 56 | 46 |
| NUCLEOSIDE ANALOGS | | | | | | | | | | | | | | | | | | | | |
| M41L | 1 | | 1 | | | | | | | | | | | | | | | | | |
| K65R | | 1 | | | | | | | | | | | | | | | | | | |
| D67N | | | | 1 | | | | | | | | | | | | | | | | |
| T69D | | 1 | | | | | | | | | | | | | | | | | | |
| K70E | | 1 | | | | | | | | | | | | | | | | | | |
| K70R | | 1 | | | | | | | | | | | | | | | | | | |
| L74V | | | | | | | 1 | | | | | | | | | | | | | |
| V75T | | | | 1 | | | | | | | | | | | | | | | | |
| Y115F | 1 | | | | | | | | | | | | | | | | | | | |
| M184I | | | | 1 | | | | | | | | | | | | | | | | |
| M184V | | 1 | | 1 | | | | | | | | 1 | | | | | | | | |

FIG 2B, part 1

| | A-T | A-G | A-C | G-A | G-C | G-T | C-A | C-G | C-T | T-A | T-G | T-C |
|---|---|---|---|---|---|---|---|---|---|---|---|---|
| L210W | | | | | | | | | | | 1 | |
| T215Y | 1 | | | | | | 1 | | | | | |
| T215C | 1 | | | | | | | | | | | |
| T215F | | | | | | | | | 1 | | 1 | |
| K219Q | | | 1 | | | | | | | | | |
| K219E | | 1 | | | | | | | | | | |
| NON NUCLEOSIDE RT INHIBITORS | | | | | | | | | | | | |
| L74I | | | | 1 | | | | | | 1 | | |
| V75L | | | | | | 1 | | | | | | |
| V75I | | | | | 1 | | | | | | | |
| A98G | | | | | | | | | | | | |
| L100I | | | | | | | | | | 1 | | |
| K101E | | 1 | | | | | | | | | | |
| K101I | 1 | | | | | | | | | | | |

FIG 2B, part 2

| | A-T | A-G | A-C | G-A | G-C | G-T | C-A | C-G | C-T | T-A | T-G | T-C |
|---|---|---|---|---|---|---|---|---|---|---|---|---|
| K101Q | | | 1 | | | | | | | | | |
| K103R | | 1 | | | | | | | | | | |
| K103T | | | 1 | | | | | | | | | |
| K103Q | | | | | | | 1 | | | | | |
| K103N | | | 1 | | | | | | | | | |
| V106I | | | | 1 | | | | | | | | |
| V106A | | | | | | | | | | | | 1 |
| V108I | | | | 1 | | | | | | | | |
| E138K | | | | 1 | | | | | | | | |
| T139I | | | | | | | | | 1 | | | |
| G141E | | | | 1 | | | | | | | | |
| V179E | | | | | | | | | | 1 | 1 | |
| V179D | | | | | | | | | | 1 | | |
| Y181C | | 1 | | | | | | | | | | |
| Y181I | | | | | | 1 | | | | 1 | | |
| Y188L | 1 | | | | | | | | | 1 | | |

FIG 2B, part 3

| | A-T | A-G | A-C | G-A | G-C | G-T | C-A | C-G | C-T | T-A | T-G | T-C |
|---|---|---|---|---|---|---|---|---|---|---|---|---|
| Y188C | | 1 | | | | | | | | | | |
| Y188H | | | | | | | | | | | | 1 |
| V189I | | | | 1 | | | | | | | | |
| G190Q | | | | 1 | 1 | | | | | | | |
| G190A | | | | | 1 | | | | | | | |
| G190E | | | | 1 | | | | | | | | |
| E233V | 1 | | | | | | | | | | | |
| P236L | | | | | | | | | 1 | | | |
| K238T | | | 1 | | | | | | | | | |

FIG 2B, part 4

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid -continued (iii) HYPOTHETICAL: no (iv) ANTI-SENSE: yes (v) FRAGMENT TYPE: internal (vi) ORIGINAL SOURCE:
              (A) ORGANISM: HIV (ix) FEATURE:
              (D) OTHER INFORMATION: amplification primer for HIV (xi) SEQUENCE DESCRIPTION: SEQ ID NO:1:

CAGAARCAGG AGCHGAWAG ACA                                                    22

(2) INFORMATION FOR SEQ ID NO: 2:

(i) SEQUENCE CHARACTERISTICS:
              (A) LENGTH: 25
              (B) TYPE: nucleic acid
              (C) STRANDEDNESS: double
              (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
              (A) ORGANISM: HIV (ix) FEATURE:
              (D) OTHER INFORMATION: amplification primer for HIV (xi) SEQUENCE DESCRIPTION: SEQ ID NO:2:

CTAYTARGTC TTTTGWTGGG TCATA                                                 25

(2) INFORMATION FOR SEQ ID NO: 3:

(i) SEQUENCE CHARACTERISTICS:
              (A) LENGTH: 22
              (B) TYPE: nucleic acid
              (C) STRANDEDNESS: double
              (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
              (A) ORGANISM: HIV (ix) FEATURE:
              (D) OTHER INFORMATION: amplification primer for HIV (xi) SEQUENCE DESCRIPTION: SEQ ID NO:3:

AAGCAGGAGC CGATAGACAA GG                                                    22

(2) INFORMATION FOR SEQ ID NO: 4:

(i) SEQUENCE CHARACTERISTICS:
              (A) LENGTH: 22
              (B) TYPE: nucleic acid
              (C) STRANDEDNESS: double
              (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
             (A) ORGANISM: HIV (ix) FEATURE:
             (D) OTHER INFORMATION: amplification primer for HIV (xi) SEQUENCE DESCRIPTION: SEQ ID NO:4:

AAGCAGGAGC TGAAAGACAG GG                                                        22

(2) INFORMATION FOR SEQ ID NO: 5:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
            (A) ORGANISM: HIV (ix) FEATURE:
            (D) OTHER INFORMATION: amplification primer for HIV (xi) SEQUENCE DESCRIPTION: SEQ ID NO: 5:

AAGCAGGAGC AGAAAGACAA GG                                                        22

(2) INFORMATION FOR SEQ ID NO: 6:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
            (A) ORGANISM: HIV (ix) FEATURE:
            (D) OTHER INFORMATION: amplification primer for HIV (xi) SEQUENCE DESCRIPTION: SEQ ID NO: 6:

CAGAAGCAGG AGCCGAWAGA CA                                                        22

(2) INFORMATION FOR SEQ ID NO: 7:

(i) SEQUENCE CHARACTERISTICS:
            (A) LENGTH: 25
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
             (A) ORGANISM: HIV (ix) FEATURE:
             (D) OTHER INFORMATION: amplification primer for HIV (xi) SEQUENCE DESCRIPTION: SEQ ID NO: 7:

CTATTAAGTC TTTTGATGGG TCATA                                           25

(2) INFORMATION FOR SEQ ID NO: 8:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
             (A) ORGANISM: HIV (ix) FEATURE:
             (D) OTHER INFORMATION: sequencing primer for HIV (xi) SEQUENCE DESCRIPTION: SEQ ID NO: 8:

GCCGATAGAC AAGGAACTG                                                  19

(2) INFORMATION FOR SEQ ID NO: 9:

(i) SEQUENCE CHARACTERISTICS:
             (A) LENGTH: 21
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
             (A) ORGANISM: HIV (ix) FEATURE:
             (D) OTHER INFORMATION: sequencing primer for HIV (xi) SEQUENCE DESCRIPTION: SEQ ID NO: 9:

ACTTTTGGGC CATCCATTCC T                                               21

(2) INFORMATION FOR SEQ ID NO: 10:

(i) SEQUENCE CHARACTERISTICS:
             (A) LENGTH: 21
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
             (A) ORGANISM: HIV (ix) FEATURE:
             (D) OTHER INFORMATION: sequencing primer for HIV (xi) SEQUENCE DESCRIPTION: SEQ ID NO: 10:

ACTTTTGGGC CATCCATCCC T                                              21

(2) INFORMATION FOR SEQ ID NO: 11:

(i) SEQUENCE CHARACTERISTICS:
             (A) LENGTH: 21
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
             (A) ORGANISM: HIV (ix) FEATURE:
             (D) OTHER INFORMATION: sequencing primer for HIV (xi) SEQUENCE DESCRIPTION: SEQ ID NO: 11:

ACCTTTGGTC CATCCATTCC T                                              21

(2) INFORMATION FOR SEQ ID NO: 12:

(i) SEQUENCE CHARACTERISTICS:
             (A) LENGTH: 26
             (B) TYPE: nucleic acid
             (C) STRANDEDNESS: double
             (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
             (A) ORGANISM: HIV (ix) FEATURE:
             (D) OTHER INFORMATION: sequencing primer for HIV (xi) SEQUENCE DESCRIPTION: SEQ ID NO: 12:

GTTAAACAAT GGCCATTGAC AGAAGA                                         26

(2) INFORMATION FOR SEQ ID NO: 13:

(i) SEQUENCE CHARACTERISTICS:
             (A) LENGTH: 24
             (B) TYPE: nucleic acid
             (C) STRANDEDNESS: double (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: HIV (ix) FEATURE:
        (D) OTHER INFORMATION: sequencing primer for HIV (xi) SEQUENCE DESCRIPTION: SEQ ID NO: 13:

GGAATATTGC TGGTGATCCT TTCC                                          24

(2) INFORMATION FOR SEQ ID NO: 14:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: HIV (ix) FEATURE:
        (D) OTHER INFORMATION: sequencing primer for HIV (xi) SEQUENCE DESCRIPTION: SEQ ID NO: 14:

GTTAAACAAT GGCCATTGAC AG                                            22

(2) INFORMATION FOR SEQ ID NO: 15:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: HIV (ix) FEATURE:
        (D) OTHER INFORMATION: sequencing primer for HIV (xi) SEQUENCE DESCRIPTION: SEQ ID NO: 15:

ATTAGATATC AGTACAATGT GC                                            22

(2) INFORMATION FOR SEQ ID NO: 16:

(i) SEQUENCE CHARACTERISTICS:
        (A) LENGTH: 24
        (B) TYPE: nucleic acid

```
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
            (A) ORGANISM: HIV (ix) FEATURE:
            (D) OTHER INFORMATION: sequencing primer for HIV (xi) SEQUENCE DESCRIPTION: SEQ ID NO: 16:

TCTGTATGTC ATTGACAGTC CAGC                                              24

(2) INFORMATION FOR SEQ ID NO: 17:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
            (A) ORGANISM: HIV (ix) FEATURE:
            (D) OTHER INFORMATION: sequencing primer for HIV (xi) SEQUENCE DESCRIPTION: SEQ ID NO: 17:

TCTGTATATC ATTGACAGTC CAGT                                              24

(2) INFORMATION FOR SEQ ID NO: 18:

(i) SEQUENCE CHARACTERISTICS:
            (A) LENGTH: 24
            (B) TYPE: nucleic acid
            (C) STRANDEDNESS: double
            (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
            (A) ORGANISM: HIV (ix) FEATURE:
            (D) OTHER INFORMATION: sequencing primer for HIV (xi) SEQUENCE DESCRIPTION: SEQ ID NO: 18:

TCTGTATATC ATTGACAGTC CAGC                                              24

(2) INFORMATION FOR SEQ ID NO: 19:

(i) SEQUENCE CHARACTERISTICS:
            (A) LENGTH: 25
```

```
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: HIV (ix) FEATURE:
        (D) OTHER INFORMATION: sequencing primer for HIV (xi) SEQUENCE DESCRIPTION: SEQ ID NO: 19:

TTCTGTATGT CATTGACAGT CCAGC                                          25

(2) INFORMATION FOR SEQ ID NO: 20:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: HIV (ix) FEATURE:
        (D) OTHER INFORMATION: sequencing primer for HIV (xi) SEQUENCE DESCRIPTION: SEQ ID NO: 20:

GACTTAGAAA TAGGGCAGCA TAGA                                           24

(2) INFORMATION FOR SEQ ID NO: 21:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: HIV (ix) FEATURE:
        (D) OTHER INFORMATION: sequencing primer for HIV (xi) SEQUENCE DESCRIPTION: SEQ ID NO: 21:

ATTAAGTCTT TTGATGGGTC ATAA                                           24

(2) INFORMATION FOR SEQ ID NO: 22:

(i) SEQUENCE CHARACTERISTICS:
```

-continued

```
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: HIV (ix) FEATURE:
        (D) OTHER INFORMATION: sequencing primer for HIV (xi) SEQUENCE DESCRIPTION: SEQ ID NO: 22:

CCATTCCTGG CTTTAATTTT ACTGG                                                25

(2) INFORMATION FOR SEQ ID NO: 23:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: HIV (ix) FEATURE:
        (D) OTHER INFORMATION: sequencing primer for HIV (xi) SEQUENCE DESCRIPTION: SEQ ID NO: 23:

ATCACTCTTT GGCAACGACC                                                      20
```

METHOD AND KIT FOR EVALUATION OF HIV MUTATIONS

This application is a continuation-in-part of U.S. patent application Ser. No. 08/577,858, filed Dec. 22, 1995, U.S. Pat. No. 5,834,189, and U.S. patent application Ser. No. 08/819,912 filed Mar. 18, 1997, U.S. Pat. No. 5,795,722, which are incorporated herein by reference.

BACKGROUND OF THE INVENTION

Genetic testing to determine the presence of or a susceptibility to a disease condition offers incredible opportunities for improved medical care, and the potential for such testing increases almost daily as ever increasing numbers of disease-associated genes and/or mutations are identified. A major hurdle which must be overcome to realize this potential, however, is the high cost of testing. This is particularly true in the case of highly polymorphic genes where the need to test for a large number of variations may make the test procedure appear to be so expensive that routine testing can never be achieved.

Testing for changes in DNA sequence can proceed via complete sequencing of a target nucleic acid molecule, although many persons in the art believe that such testing is too expensive to ever be routine. Changes in DNA sequence can also be detected by a technique called "single-stranded conformational polymorphism" ("SSCP") described by Orita et al., *Genomics* 5:874–879 (1989), or by a modification thereof referred to a dideoxy-fingerprinting ("ddF") described by Sarkar et al., *Genomics* 13:4410443 (1992). SSCP and ddF both evaluate the pattern of bands created when DNA fragments are electrophoretically separated on a non-denaturing electrophoresis gel. This pattern depends on a combination of the size of the fragments and of the three-dimensional conformation of the undenatured fragments. Thus, the pattern cannot be used for sequencing, because the theoretical spacing of the fragment bands is not equal.

The hierarchical assay methodology described in U.S. Pat. No. 5,545,527 and International Patent Publication No. WO 96/07761, which are incorporated herein by reference, provides a mechanism for systematically reducing the cost per test by utilizing a series of different test methodologies which may have significant numbers of results incorrectly indicating the absence of a genetic sequence of interest, but which rarely if ever yield a result incorrectly indicating the presence of such a genetic sequence. The tests employed in the hierarchy may frequently be combinations of different types of molecular tests, for examples combinations of immunoassays, oligonucleotide probe hybridization tests, oligonucleotide fragment analyses, and direct nucleic acid sequencing.

This application relates to a particular series of tests which can be useful alone or as part of a hierarchical testing protocol for the detection and characterization of human immunodeficiency virus (HIV).

SUMMARY OF THE INVENTION

The method of the invention provides a streamline, hierarchical method for obtaining information about the allelic type of a sample of genetic material derived from an HIV-infected sample. It has been determined that 93 to 95% of the known mutational variants of the protease and reverse transcriptase genes of HIV can be determined by evaluating the positions of the A and T nucleotides within the sample. Thus, a substantial fraction of all mutational variations can be unequivocally identified by performing two initial sequencing reactions on the sample in which only ddA and ddT are used as chain terminators. For the small fraction of samples which are not identifiable based on the positions of these two bases, a second test is performed in which the sequence is determined in the 3'-direction for all four bases. This test will identify substantially all of the remaining samples. For those for which an ambiguity remains, however, a final test in which the sequence of the sample is determined in both the 3' and 5-direction for all four bases is performed.

To perform the method of the invention, reagents suitable for performing the three tests within the hierarchy are suitably packages as a kit containing two or more sub-kits. The first sub-kit contains reagents for performing A and T sequencing. The addition sub-kit(s) contains reagents for performing a four-base sequence determination on one or both strands of the target DNA. One-stranded sequence determination could be performed all in the 3'-direction, all in the 5'-direction, or as a combination of the two strands.

BRIEF DESCRIPTION OF THE DRAWINGS

FIGS. 2A and 2B shows the bases which are changed in known mutations of the protease and reverse transcriptase genes of HIV-1.

DETAILED DESCRIPTION OF THE INVENTION

Figure 1:
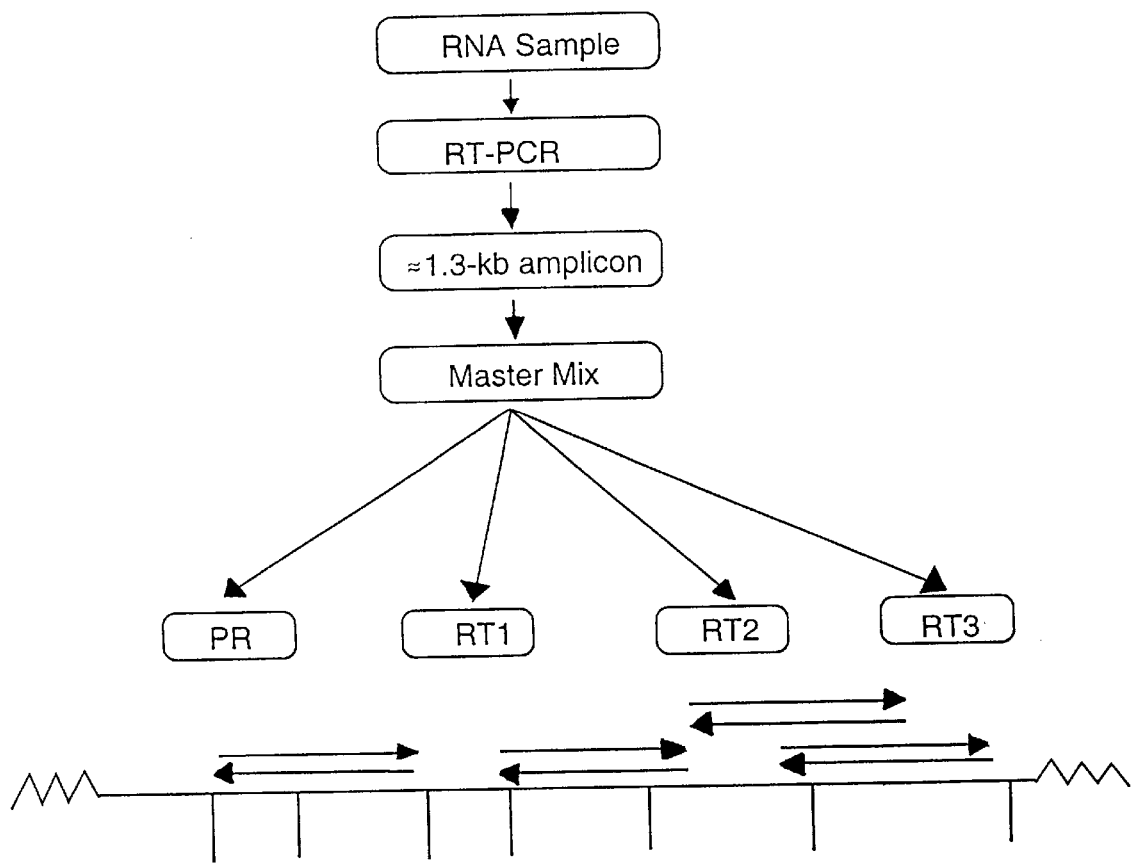
FIG. 1 shows a schematic representation of the invention.

While the terminology used in this application is standard within the art, the following definitions of certain terms are provided to assure clarity.

1. "Allele" refers to a specific version of a nucleotide sequence at a polymorphic genetic locus.
2. "Polymorphic site" means a given nucleotide location in a genetic locus which is variable within a population.
3. "Gene" or "Genetic locus" means a specific nucleotide sequence within a given genome.
4. The "location" or "position" of a nucleotide in a genetic locus means the number assigned to the nucleotide in the gene, generally taken from the cDNA sequence or the genomic sequence of the gene.
5. The nucleotides Adenine, Cytosine, Guanine and Thymine are sometimes represented by their designations of A, C, G or T, respectively. Dideoxynucleotides which are used as chain terminators are abbreviated as ddA, ddC, ddG and ddT.

While it has long been apparent to persons skilled in the art that knowledge of the identity of the base at a particular location within a polymorphic genetic locus may be sufficient to determine the allelic type of that locus, this knowledge has not led to any modification of sequencing procedures. Rather, the knowledge has driven development of techniques such as allele-specific hybridization assays, and allele-specific ligation assays. Despite the failure of the art to recognize the possibility, however, it is not always necessary to determine the sequence of all four nucleotides of a polymorphic genetic locus in order to determine which allele is present in a specific patient sample. As disclosed generally in International Patent Publication No. WO 97/23650, certain alleles of a genetic locus may be distinguishable on the basis of identification of the location of less than four, and often only one nucleotide. This finding allows the development of the present method for improved allele identification within the highly polymorphic HIV genome.

Traditionally, if sequencing were going to be used to evaluate the allelic type of a polymorphic gene, four dideoxy nucleotide "sequencing" reactions of the type described by Sanger et al. (Proc. Natl. Acad. Sci. USA 74: 5463–5467 (1977)) would be run on the sample concurrently, and the products of the four reactions would then be analyzed by polyacrylamide gel electrophoresis. (see Chp 7.6, Current Protocols in Molecular Biology, Eds. Ausubel, F. M. et al, (John Wiley & Sons; 1995)) In this well-known technique, each of the four sequencing reactions generates a plurality of primer extension products, all of which end with a specific type of dideoxynucleotide. Each lane on the electrophoresis gel thus reflects the positions of one type of base in the extension product, but does not reveal the order and type of nucleotides intervening between the bases of this specific type. The information provided by the four lanes is therefore combined in known sequencing procedures to arrive at a composite picture of the sequence as a whole.

In the method of the invention the sequence of a good portion of the diagnostically relevant protease and reverse transcriptase genes is obtained in three steps: 1) cDNA is generated from the RNA present in the sample, and amplified, preferably across a region extending from 6 condons before the protease up to codon 335 of the reverse transcriptase of HIV-1 (the primer regions are not included in this range). 2) Sequencing reactions are performed at one or more of several hierarchical levels. 3) Finally, the sequencing ladders are analyzed, preferably using the Open-Gene™ System: the Micro GeneBlaster™ DNA Sequencer, GeneObjects™ and GeneLibrarian™ Softwares.

FIG. 1 shows one embodiment of the method of the invention schematically. As shown, an RNA sample is obtained and treated by reverse transcriptase-PCR (RT-PCR) to produce an amplicon of approximately 1.3 kbase pairs spanning the protease and reverse transcriptase genes of the HIV genome from a target cell. This reaction can be performed using, for example, the TITAN™ One-Tube RT-PCR system from Boehringer Mannheim (Cat. No. 1 855 476 or 1 882 382) using the following primers:
CAGAARCAGG AGCHGAWAG ACA [Seq.1] (forward)
CTAYTARGTC TTTTGWTGG GTCATA [Seq.2] (reverse)
Other primers which could be used at this step include:
forward primers:
AAGCAGGAGC CGATAGACAA [Seq.3] GG
AAGCAGGAGC TGAAAGACAG [Seq.5] GG
AAGCAGGAGC AGAAAGACAA [Seq.5] GG
reverse primers:
CAGAAGCAGG AGCCGAWAGA CA [Seq.6]
CTATTAAGTC TTTTGATGGG TCATA [Seq.7]

This amplicon is then combined with a master sequencing mixture containing buffer (260 mM Tris-HCL, pH 8.3; 32.5 mM MgCl$_2$) and a polymerase enzyme such as Taq FS (Perkin Elmer/Applied Biosystems Cat No. 402070) This polymerase has a high rate of incorporation of dideoxy-nucleotide relateive to the incorporation rate of, for example, conventional Taq polymerase. This mixture is used as stock in the subsequent reactions.

The first sequencing reaction performed in the method of the invention is a single-base sequencing reaction performed using either ddA or ddT in the sequencing mixture. This reaction is performed on the protease gene using the following primers:
forward primer:
GCCGATAGAC AAGGAACTG [Seq.8]
REVERSE PRIMER
ACTTTTGGGC CATCCATTCC T [Seq.9]
Alternate reverse primers which may be used are:
ACTTTTGGGC CATCCATCCC T [Seq.10]
ACCTTTGGTC CATCCATTCC T [Seq.11]
For the reverse transcriptase gene, three sets of primers are used as follows:
RT1 Primers
forward:
GTTAAACAAT GGCCATTGAC AGAAGA [Seq.12]
reverse:
GGAATATTGC TGGTGATCCT TTCC [Seq.13]
alternate forward:
GTTAAACAAT GGCCATTGAC AG [Seq.14]
RT2 Primers
forward:
ATTAGATATC AGTACAATGT GC [Seq.15]
reverse:
TCTGTATGTC ATTGACAGTC CAGC [Seq.16]
alternate reverse:
TCTGTATATC ATTGACAGTC CAGT [Seq.17]
TCTGTATATC ATTGACAGTC CAGC [Seq.18]
TTCTGTATGT CATTGACAGT CCAGC [Seq.19]
RT3 Primers
forward:
GACTTAGAAA TAGGGCAGCA TAGA [Seq.20]
reverse:
ATTAAGTCTT TTGATGGGTC ATAA [Seq.21]

When a sequencing device is employed which is capable of detecting and distinguishing two different fluorescent dyes (such as, for example, the ABI Prism Models 377, 310 or 373 or LiCor IR$^2$System), both the forward and reverse primers are preferably each labeled with one of the two dyes. Forward and reverse sequencing fragments are then generated by thermally cycling the sample through multiple thermal cycles in the presence of either ddA or ddT. Analysis of the sequencing fragments produced using gel electrophoresis will allow the determination of the positions of both A and T bases. As shown in FIGS. 2A and B, knowledge of the position of the A and T bases will identify 95% of all known mutational variants within the reverse transcriptase gene and 93% of the variants within the protease gene. Thus, by performing a single reaction, the allelic type of majority of samples can be identified.

If the sequencer employed is only capable of evaluating a single base, then two reaction need to be employed. These may be a forward and backwards sequencing reaction both employing the same chain terminator (ddA or ddT), or two reaction performed in the same direction, one with ddA and one with ddT so that the positions of A and T bases are determined. These sequencing reactions can be employed using the same primers discussed above.

If the type of the HIV present in the sample cannot determined based upon the results of the first reaction, then a further sequencing reaction is performed on the sample stock to determine the positions of all four bases. Preferably, this is a sequencing reaction of intermediate complexity, involving the sequencing of one of the two strands of the DNA or a combination of the two strands making up one complete linear sequence. This can be done using the same primers identified above to obtain sequencing fragments.

Finally, if the intermediate test fails to provide unambiguous identification of the DNA type, sequencing of both strands may be performed. Again, the same sequencing primers identified above are used. Forward and reverse sequencing fragments can be produced in a single reaction using distinctively labeled forward and reverse primers, or in separate reactions depending on the nature of the detection system being employed.

Reagents suitable for practicing the method of the invention are suitably packaged in kit form. Thus, the invention provides a kit for analyzing the genetic type of an HIV-1 gene in a sample using a hierarchical assay comprising, in separately packed combinations:

(a) a first subkit for performing A and T sequencing on HIV-1, comprising a plurality of A or T terminations mixtures, or both A and T termination mixtures, but no G termination mixture or C termination mixture, each of said A and T termination mixtures including one of a plurality of primer pairs, each pair flanking a different region of the HIV-1 genome, the pairs together flanking substantially all of the protease and reverse transcriptase genes, and at least one member of each pair being labeled with a detectable label; and (b) a second subkit for performing four base sequencing on HIV-1 comprising a plurality of A, C, G and T terminations mixtures, each of said termination mixtures including one of a plurality of primer pairs, each pair flanking a different region of the HIV-1 genome, the pairs together flanking substantially all of the protease and reverse transcriptase genes, and at least one member of each pair being labeled with a detectable label. Additional subkits for performing four base sequencing may be included when intermediate and final assays on one strand and both strands are desired.

As used herein, the term "termination mixture" refers to a mixture containing a mixture of the four deoxunucleotide triphosphates (dATP, dCTP, dGTP, and dTTP), one species of chain terminating dideoxynucleotide (ddATP, ddCTP, ddGTP or ddTTP) and the appropriate sequencing primers.

The subkit for performing A and T sequencing on HIV-1 may also be provided separately for performing the initial determination of only the A and T nucleotides. A preferred kit of this type, whether provided separately or as part of a kit for performing a hierarchical assay has primer pairs in which each primer is labeled with a different an spectroscopically distinguishable fluorescent dye, such as Cy5.0 and Cy5.5 and includes only one of the two possible types of termination mixtures, for example just the T termination mixture.

The following examples are included to illustrate aspects of the instant invention and are not intended to limit the invention in any way.

EXAMPLE 1

The variety or sub-type of HIV can be determined by Single Track Sequencing of a sample which has been amplifed by RT-PCR.

A reaction mixture is prepared as follows:
3 ul bound beads
3 ul sequencing primer (30 ng total)
2 ul 13X sequencing buffer (260 mM Tris-HCL, pH 9.5, 39 mM MgCl$_2$)
2 ul Thermo Sequenase (Amersham Life Sciences, Cleveland) ((diluted 1:10 from stock to 3.2 U/ul)
3 ul distilled H2O
Final Volume: 13 ul The sequencing primer employed is the non-biotinylated primer of the sequencing template amplification reaction, but this time it is labeled with a detectable label. The preferred label for detection on the MicroGene Blaster is Cy5.5 linked to the 5' nucleotide of the primer.
CCATTCCTGG CTTTAATTTT ACTGG [Seq.22]

The reaction mixture is kept on ice. A single chain termination reaction mixture, in this case for the T nucleotide, is prepared by combining 750 uM of each of dATP, cDTP, dGTP and dTTP; and 2.5 uM of ddTTP. 3 ul of the termination reaction mix is place in a tube. 3 ul of the sequencing reaction mixture is added. An oil overlay is added and the single track reaction mixture is heated to 95° C. for 2 mins in a PTC-100 Programmable Thermal Controller (MJ Reasearch, Inc.) or Robocycler Gradient 96 (Stratagene) before being thermally processed for 25 cycles (or fewer if found to be satisfactory) as follows:
Annealing: 50° C. for 10 Sec.
Extension: 70° C. for 30 Sec.
Denaturation: 95° C. for 30 Sec.

After a final extension at 70° C. for 5 min the sample is denatured at 95° C. for 30 secs and left on ice. The sample is mixed with 6 ul of STOP/Loading buffer containing 100% formamide and 5 mg/ml dye such as dextran blue.

1.5 ul of the mixture is loaded on a single lane of a MICROGENE BLASTER (Visible Genetics Inc., Toronto) and reaction products are separated by electrophoresis through a denaturing polyacrylamide gel. The reaction products are detected and presented with GENEOBJECTS software (Visible Genetics Inc., Toronto). The finger-print or bar-code of the reaction products is compared to all known varieties of the pathogen nucleic acid sequence. An exact match is sought. If only one match is found, that subtype or variety is positively identified. If the patient sample had mixed varieties the result may show a heterogenous mix. The members of the heterogenous mix and relative quantities may be determined.

EXAMPLE 2

The variety or sub-type of the pathogen can be determined using CLIP™ sequencing methodology. In this method the sequence of both the sense strand and antisense strand of the protease gene of HIV-1 may be obtained in a one step reaction as follows.

Combine the following materials and mix well:

|  | Concentration | Volume |
| --- | --- | --- |
| Sequencing fragment DNA |  | 3 ul |
| PR211*Cy5.5 Primer | .10 uM | 0.5 ul |
| PR526*Cy5.0 Primer | 10 uM | 0.5 ul |
| diluted Thermosequenase Enzyme | 3.2 U/ul | 2 ul |
| 13 X Reaction buffer |  | 2 ul |
| double distilled H2O |  | 5 ul |
| TOTAL VOLUME |  | 13.0 ul |

13X reaction buffer consists of Tris-HCL 260 mM pH 8.3, MgCl$_2$39 mM.
PR211 ATCACTCTTT GGCAACGACC [Seq 23]
PR526: CCATTCCTGG CTTTAATTTT ACTGG [Seq 22]

Place 3 ul of mixture into each of 4 tubes. Heat tubes to 94° C. for 5 mins then reduce temperature to 85° C. Add and mix 3 ul of an 85° C. dNTP/ddNTP solution containing 0.75 mM each dNTP and 2.5 uM of a chain terminating nucleotide triphosphate (ddNTP) (use a different ddNTP in each of the 4 tubes).

Treat the mixture to 60 cycles of the following thermal cycling reactions: 94° C. for 10 sec, 62° C. for 15 sec, 70° C. for 1 min. Upon completion, treat the mixture for a final 5 min at 70° C. and then store at 4° C. until ready for loading. For viewing the reaction products, add an equal volume of stop/loading solution (95% formamide plus a colored dye). Take 1.5 ul and load in a single lane of a two dye MicroGene Blaster automated DNA sequencer (Visible Genetics Inc., Toronto).

The reaction products from the both labeled primers are detected on the MICROGENE BLASTER as two separate traces, and displaced on GENEOBJECTS Software.

The base-called results from each primer were compared to the known protease gene sequences of HIV-1 and -2 by GENELIBRARIAN (a component of GENEOBJECTS (Visible Genetics Inc., Toronto). The sub-type of HIV-1 or HIV-2 is determined, and the presence of drug resistance codons is determined. Once the sequence of the HIV sub-type(s) is determined, it is reported to the patient file along with the quantitation data.

EXAMPLE 3

The RT-PCR is done on the HIV-1 RNA using the Titan™ One Tube RT-PCR System from Boehringer Mannheim. This RT-PCR is done on the RNA preparation obtained using the Amplicor™ HIV Monitor Test from Roche Diagnostic. It can also be done on the RNA extract for the NucliSense™ (formerly known as NASBA) HIV Viral Load from Organon Teknica.

All the reagents, tubes, tips, and other material needs to be RNase-free. The recipe is made for 8 reactions (one strip of 8 tubes), including 10% extra. Thaw the RNA sample from the Amplicor HIV Monitor Test and keep on ice. This is the material obtained at step 14 of the section B "Specimen Preparation". If using RNA prepared for the NucliSense Assay, proceed the same way: thaw it and keep it on ice.

Take a 0.2 ml sterile, RNase-free, centrifuge tube, RNase-free, and prepare the RT-PCR Master Mix I (enough for 8 tubes, including 10% extra) by adding the following ingredient in the order listed:
RT-PCR MASTER MIX I
35 $\mu$l of 100 mM DTT
13 $\mu$l of RNase-free dNTP @ 10 mM each dNTP
13 $\mu$l of forward PCR primer at 10 $\mu$M
13 $\mu$l of reverse PCR primer at 10 $\mu$M Take a 0.2 ml sterile, RNase-free, centrifuge tube, RNase-free, and prepare the RT-PCR Master Mix II (enough for 8 tubes, including 20% extra) by adding the following ingredient in the order listed:
RT-PCR MASTER MIX II
60 $\mu$l of Titan 5X Buffer
5 $\mu$l of RNase Inhibitor @ 40 U/$\mu$l
10 $\mu$l of Titan Enzyme
18 $\mu$l of RNase-free MgCl2 at 25 mM
7 $\mu$l of RNase-free water Take one strip of 8 thin wall tubes. Add 8.5 $\mu$l of MASTER MIX I in each tube. Add 11.5 $\mu$l of sample (RNA) to each tube. You may want to add a negative control per experiment. If using RNA extracted for the NucliSense Assay, dilute the sample 1:5 in RNase-free water and use 11.5 $\mu$l of this dilution.

Heat the RNA sample at 90° C. for 3 min. using the program below:, cool at 50° C. and add 10 $\mu$l of the MASTER MIX II in each tube (step 2 of the program below). Be careful not to cross contaminate your samples.

Start the RT-PCR. Use the heated lid. When using the MJ-Plates, indicates that tubes are used when asked by the PTC-200. The following is the programming for the PTC-200:
Calculated
1=90.0° for 3:00
1=50.0° for 5:00
3=42.0°, 1:00:00
4=94.0° for 3:00
5=1.0°/s to 94.0°
6=94.0° for 0:20
7=1.0°/s to 57.0°
8=57.0° for 0:30
9=1.0°/s to 68.0°
10=68.0° for 2:30
11=Goto 5, 19 times
12=1.0°/s to 94.0°
13=94.0° for 0:20
14=1.0°/s to 57.0°
15=57.0° to 0:30
16=1.0°/s to 68.0°
17=68.0° for 3:00
18=Goto 12, 24 times
19=68.0° for 7:00
20=4.0° for ever
21=End
Store at −20° C. or keep at 4° C. and use immediately.

EXAMPLE 4

To determine the sequence of amplicon, 7 $\mu$l of each terminator mix (32 mixes when using a single dye instrument, 4 when using a two dye instrument) are combined with a 5 ul of a master mix as follows:
MASTER MIX (single dye system))
37 $\mu$l of buffer (260 mM Tris-HCl, pH 8.3, 32.5 mM MgCl2)
145 $\mu$l of sterile water
8 $\mu$l of undiluted TAQ FS 12 U/$\mu$l
10 $\mu$l of the PCR product from Example 3
MASTER MIX (two-dye system)
18.5 $\mu$l of buffer
72.5 $\mu$l of sterile water
4 $\mu$l of undiluted TAQ FS 12 U/$\mu$l
5 $\mu$l of the PCR product from Example 3

The two mixtures are mixed gently with a pipette tip. Add 8 $\mu$l of oil in each tube (optional), and start the thermocylcing reaction. The following is the programming for the PTC-200:
Calculated
1=94.0° for 5:00
2=1.0°/s to 94.0°
3=94.0° for 0:20
4=1.0°/s to 56.0°
5=56.0° for 0:20
6=1.0°/s to 70.0°
7=70.0° for 1:30
8=Goto 2, 47 times
9=70.0° for 5:00
10=4.0° for ever
11=End The following master mixes are used in this example.
Termination mix for the protease—one dye system.
A-Mix: 1.07 $\mu$M ddATP; 643 $\mu$M dATP; 643 $\mu$M dCTP; 643 $\mu$M dGTP; 643 $\mu$M dTTP;
330 nM each of forward and reverse primers
C-Mix: 2.14 $\mu$M ddCTP; 643 $\mu$M dATP; 643 $\mu$M dCTP; 643 $\mu$M dGTP; 643 $\mu$M dTTP;
330 nM each of forward and reverse primers
G-Mix: 2.14 $\mu$M ddGTP; 643 $\mu$M dATP; 643 $\mu$M dCTP; 643 $\mu$M dGTP; 643 $\mu$M dTTP;
330 mM each of forward and reverse primers
T-Mix: 2.14 $\mu$M ddTTP; 643 $\mu$M dATP; 643 $\mu$M dCTP; 643 $\mu$M dGTP; 643 $\mu$M dTTP;
330 nM each of forward and reverse primers
One primer in each pair is labeled.
Termination mix for the first region of reverse transcriptase—(one dye system)
A-Mix: 1.07 $\mu$M ddATP; 643 $\mu$M dATP; 643 $\mu$M dCTP; 643 $\mu$M dGTP; 643 $\mu$M dTTP;
330 nM each of forward and reverse primers
C-Mix: 2.14 $\mu$M ddCTP; 643 $\mu$M dATP; 643 $\mu$M dCTP; 643 $\mu$M dGTP; 643 M dTTP;

330 nM each of forward and reverse primers
G-Mix: 2.14 μM ddGTP; 643 μM dATP; 643 μM dCTP; 643 μM dGTP; 643 M dTTP;
330 nM each of forward and reverse primers
T-Mix: 2.14 μM ddGTP; 643 μM dATP; 643 μM dCTP; 643 μM dGTP; 643 M dTTP;
330 nM each of forward and reverse primers
One primer of each pair is labeled.
Termination mix for the second region of reverse transcriptase (one dye system)
A-Mix: 1.07 μM ddATP; 643 μM dATP; 643 μM dCTP; 643 μM dGTP; 643 μM dTTP;
330 nM each of forward and reverse primers
C-Mix: 2.14 μM ddCTP; 643 μM dATP; 643 μM dCTP; 643 μM dGTP; 643 M dTTP;
330 nM each of forward and reverse primers
G-Mix: 2.14 μM ddGTP; 643 μM dATP; 643 μM dCTP; 643 μM dGTP; 643 M dTTP;
330 nM each of forward and reverse primers
T-Mix: 2.14 μM ddGTP; 643 μM dATP; 643 μM dCTP; 643 μM dGTP; 643 M dTTP;
330 nM each of forward and reverse primers
One primer of each pair is labeled.
Termination mix for the third region of the reverse transcriptase (single dye system)
A-Mix: 1.07 μM ddATP; 643 μM dATP; 643 μM dCTP; 643 μM dGTP; 643 μM dTTP;
330 nM each of forward and reverse primers
C-Mix: 2.14 μM ddCTP; 643 μM dATP; 643 μM dCTP; 643 μM dGTP; 643 M dTTP;
330 nM each of forward and reverse primers
G-Mix: 2.14 μM ddGTP; 643 μM dATP; 643 μM dCTP; 643 μM dGTP; 643 M dTTP;
330 nM each of forward and reverse primers
T-Mix: 2.14 μM ddGTP; 643 μM dATP; 643 μM dCTP; 643 μM dGTP; 643 M dTTP;
330 nM each of forward and reverse primers
One dye in each reaction is labeled.
Termination mixes for two dye systems
Protease
A-Mix: 1.07 μM ddATP; 643 μM dATP; 643 μM dCTP; 643 μM dGTP; 643 μM dTTP;
330 nM each of forward and reverse primers
C-Mix: 2.14 μM ddCTP; 643 μM dATP; 643 μM dCTP; 643 μM dGTP; 643 M dTTP;
330 nM each of forward and reverse primers
G-Mix: 2.14 μM ddGTP; 643 μM dATP; 643 μM dCTP; 643 μM dGTP; 643 M dTTP;
330 nM each of forward and reverse primers
T-Mix: 2.14 μM ddGTP; 643 μM dATP; 643 μM dCTP; 643 μM dGTP; 643 M dTTP;
330 nM each of forward and reverse primers
Both primers are labeled, for example with Cy5.0 and Cy5.5, respectively.
First RT region
A-Mix: 1.07 μM ddATP; 643 μM dATP; 643 μM dCTP; 643 μM dGTP; 643 μM dTTP;
330 nM each of forward and reverse primers
C-Mix: 2.14 μM ddCTP; 643 μM dATP; 643 μM dCTP; 643 μM dGTP; 643 M dTTP;
330 nM each of forward and reverse primers
G-Mix: 2.14 μM ddGTP; 643 μM dATP; 643 μM dCTP; 643 μM dGTP; 643 M dTTP;
330 nM each of forward and reverse primers
T-Mix: 2.14 μM ddGTP; 643 μM dATP; 643 μM dCTP; 643 μM dGTP; 643 M dTTP;
330 nM each of forward and reverse primers
Both primers are labeled, for example with Cy5.0 and Cy5.5, respectively.
Second reverse transcriptase region
A-Mix: 1.07 μM ddATP; 643 μM dATP; 643 μM dCTP; 643 μM dGTP; 643 μM dTTP;
330 nM each of forward and reverse primers
C-Mix: 2.14 μM ddCTP; 643 μM dATP; 643 μM dCTP; 643 μM dGTP; 643 M dTTP;
330 nM each of forward and reverse primers
G-Mix: 2.14 μM ddGTP; 643 μM dATP; 643 μM dCTP; 643 μM dGTP; 643 M dTTP;
330 nM each of forward and reverse primers
T-Mix: 2.14 μM ddGTP; 643 μM dATP; 643 μM dCTP; 643 μM dGTP; 643 M dTTP;
330 nM each of forward and reverse primers
Both primers are labeled, for example with Cy5.0 and Cy5.5, respectively.
Third reverse transcriptase region
A-Mix: 1.07 μM ddATP; 643 μM dATP; 643 μM dCTP; 643 μM dGTP; 643 μM dTTP;
330 nM each of forward and reverse primers
C-Mix: 2.14 μM ddCTP; 643 μM dATP; 643 μM dCTP; 643 μM dGTP; 643 M dTTP;
330 nM each of forward and reverse primers
G-Mix: 2.14 μM ddGTP; 643 μM dATP; 643 μM dCTP; 643 μM dGTP; 643 M dTTP;
330 nM each of forward and reverse primers
T-Mix: 2.14 μM ddGTP; 643 μM dATP; 643 μM dCTP; 643 μM dGTP; 643 M dTTP;
330 nM each of forward and reverse primers
Both primers are labeled, for example with Cy5.0 and Cy5.5, respectively.

We claim:

1. A method for determining the genetic type of HIV-1 present in a sample containing HIV-1, said HIV-1 having protease and reverse transcriptase genes comprising the steps of
   (a) determining the positions of just the A and T nucleotides within the protease and reverse transcriptase genes and comparing these positions to the positions of the A and T nucleotides in known genetic types;
   (b) if step (a) does not provide an unambiguous identification performing a further sequencing reaction in which the position of all four bases are determined.

2. The method of claim 1, wherein the positions of just the A and T nucleotides are determined by performing a cycled reaction that generates both forward and reverse sequencing fragments using two primers, each primer labeled with a different and distinguishable detectable label.

3. The method of claim 2, wherein the label is a fluorescent label.

4. A kit for performing A and T sequencing on an HIV-1 gene, said HIV-1 gene having protease and reverse transcriptase genes comprising a plurality of A or T termination mixtures, or both A and T termination mixtures, but no G termination mixture or C termination mixture, each of said A and T termination mixtures including one of a plurality of primer pairs, each pair flanking a different region of the HIV-1 genome, the pairs together flanking substantially all of the protease and reverse transcriptase genes, and at least one member of each pair being labeled with a detectable label.

5. The kit according to claim 4, wherein the primers include a primer pair for sequencing of the protease gene comprising a forward primer of the sequence
GCCGATAGAC AAGGAACTG [Seq.8]
and a reverse primer selected form the group consisting of
ACTTTTGGGC CATCCATTCC T [Seq.9]
ACTTTTGGGC CATCCATCCC T [Seq.10]
and
ACCTTTGGTC CATCCATTCC T [Seq.11].

6. The kit according to claim 5, wherein the primers include a primer pair for sequencing of a portion of the reverse transcriptase gene comprising a forward primer selected from the group consisting of
GTTAAACAAT GGCCATTGAC AGAAGA [Seq.12]
and
GTTAAACAAT GGCCATTGAC AG [Seq.14]
and a reverse primer having the sequence
GGAATATTGC TGGTGATCCT TTCC [Seq.13].

7. The kit according to claim 6, wherein the primers include a primer pair for sequencing of a portion of the reverse transcriptase gene comprising a forward primer having the sequence
ATTAGATATC AGTACAATGT GC [Seq.15]
and a reverse primer selected from the group consisting of
TCTGTATGTC ATTGACAGTC CAGC [Seq.16]
TCTGTATATC ATTGACAGTC CAGT [Seq.17]
TCTGTATATC ATTGACAGTC CAGC [Seq.18]
and
TTCTGTATGT CATTGACAGT CCAGC [Seq.19].

8. The kit according to claim 7, wherein the primers include a primer pair for sequencing of a portion of the reverse transcriptase gene comprising a forward primer having the sequence
GACTTAGAAA TAGGGCAGCA TAGA [Seq.20]
and a reverse primer having the sequence
ATTAAGTCTT TTGATGGGTC ATAA [Seq.21].

9. The kit according to claim 4, wherein the primers include a primer pair for sequencing of a portion of the reverse transcriptase gene comprising a forward primer having the sequence
GACTTAGAAA TAGGGCAGCA TAGA [Seq.20]
and a reverse primer having the sequence
ATTAAGTCTT TTGATGGGTC ATAA [Seq.21].

10. The kit according to claim 9, wherein the primers include a primer pair for sequencing of a portion of the reverse transcriptase gene comprising a forward primer having the sequence
ATTAGATATC AGTACAATGT GC [Seq.15]
and a reverse primer selected from the group consisting of
TCTGTATGTC ATTGACAGTC CAGC [Seq.16]
TCTGTATATC ATTGACAGTC CAGT [Seq.17]
TCTGTATATC ATTGACAGTC CAGC [Seq.18]
and
TTCTGTATGT CATTGACAGT CCAGC [Seq.19].

11. The kit according to claim 9, wherein the primers include a primer pair for sequencing of a portion of the reverse transcriptase gene comprising a forward primer selected from the group consisting of
GTTAAACAAT GGCCATTGAC AGAAGA [Seq.12]
and
GTTAAACAAT GGCCATTGAC AG [Seq.14]
and a reverse primer having the sequence
GGAATATTGC TGGTGATCCT TTCC [Seq.13].

12. The kit according to claim 4, wherein the primers include a primer pair for sequencing of a portion of the reverse transcriptase gene comprising a forward primer having the sequence
ATTAGATATC AGTACAATGT GC [Seq.15]
and a reverse primer selected from the group consisting of
TCTGTATGTC ATTGACAGTC CAGC [Seq.16]
TCTGTATATC ATTGACAGTC CAGT [Seq.17]
TCTGTATATC ATTGACAGTC CAGC [Seq.18]
and
TTCTGTATGT CATTGACAGT CCAGC [Seq.19].

13. The kit according to claim 4, wherein the primers in each primer pair are labeled with different and spectroscopically distinguishable fluorescent labels.

14. A kit for analyzing the genetic type of an HIV-1 gene in a sample using a hierarchical assay comprising, in separately packed combinations:

(a) a first subkit for performing A and T sequencing on HIV-1, said HIV-1 having protease and reverse transcriptase genes comprising a plurality of A or T terminations mixtures, or both A and T termination mixtures, but no G termination mixture or C termination mixture, each of said A and T termination mixtures including one of a plurality of primer pairs, each pair flanking a different region of the HIV-1 genome, the pairs together flanking substantially all of the protease and reverse transcriptase genes, and at least one member of each pair being labeled with a detectable label; and (b) a second subkit for performing four base sequencing on HIV-1 comprising a plurality of A, C, G and T terminations mixtures, each of said termination mixtures including one of a plurality of primer pairs, each pair flanking a different region of the HIV-1 genome, the pairs together flanking substantially all of the protease and reverse transcriptase genes, and at least one member of each pair being labeled with a detectable label.

15. The kit according to claim 14, wherein the primers in each primer pair are labeled with different and spectroscopically distinguishable fluorescent labels.

* * * * *